US012472101B2

(12) United States Patent
Lindell et al.

(10) Patent No.: US 12,472,101 B2
(45) Date of Patent: Nov. 18, 2025

(54) CABLE COMPACTION SYSTEM FOR PROTECTIVE PERSONAL EQUIPMENT

(71) Applicant: 3M INNOVATIVE PROPERTIES COMPANY, St. Paul, MN (US)

(72) Inventors: Morgan S. Lindell, Värnamo (SE); Ulf Claesson, Värnamo (SE); Robert Karlsson, Bredaryd (SE); Johan F. Hakansson, Växjö (SE); Hans-Gerd Vollmers, Cologne (DE); Niklas D. B. Emilsson, Rydaholm (SE)

(73) Assignee: 3M Innovative Properties Company, St. Paul, MN (US)

( * ) Notice: Subject to any disclaimer, the term of this patent is extended or adjusted under 35 U.S.C. 154(b) by 154 days.

(21) Appl. No.: 17/758,426

(22) PCT Filed: Jan. 14, 2021

(86) PCT No.: PCT/IB2021/050250

§ 371 (c)(1),
(2) Date: Jul. 6, 2022

(87) PCT Pub. No.: WO2021/148908

PCT Pub. Date: Jul. 29, 2021

(65) Prior Publication Data

US 2023/0023459 A1 Jan. 26, 2023

Related U.S. Application Data

(60) Provisional application No. 62/963,765, filed on Jan. 21, 2020.

(51) Int. Cl.
*H04R 1/10* (2006.01)
*A61F 11/14* (2006.01)

(52) U.S. Cl.
CPC .......... *A61F 11/145* (2022.01); *H04R 1/1033* (2013.01); *H04R 1/1083* (2013.01)

(58) Field of Classification Search
CPC ...... A61F 11/145; A61F 11/14; H04R 1/1033; H04R 1/1083; H04R 1/105; H04R 1/1066; H04R 2201/107
(Continued)

(56) References Cited

U.S. PATENT DOCUMENTS 941,798 A 11/1909 Moore
6,151,717 A 11/2000 Lindgren et al.
(Continued)

FOREIGN PATENT DOCUMENTS

EM 0080442910001 7/2020
EP 3123739 B1 * 12/2018 ........... H04R 1/1033
(Continued)

OTHER PUBLICATIONS

International Search Report for PCT International Application No. PCT/IB2021/050250, mailed on Jun. 15, 2021, 6 pages.
(Continued)

*Primary Examiner* — Carolyn R Edwards
*Assistant Examiner* — Friedrich Fahnert
(74) *Attorney, Agent, or Firm* — Katherine M. Scholz; Jonathan V. Sry

(57) ABSTRACT

A hearing protection device is presented. The device has a first earmuff connected to a second earmuff by a connector. Each of the first and second earmuffs are configured to receive an ambient sound and provide a dampened ambient sound to a wearer. The device also has a cable, with a cable length, that extends from the first earmuff to the second earmuff. The cable is coupled to the connector by a connection assembly. The connection assembly comprises a plurality of connection mechanisms arranged in a connec-
(Continued)

tion plan. Such a hearing protection device gives more freedom of placing the cable in a compact arrangement.

12 Claims, 11 Drawing Sheets

(58) Field of Classification Search
USPC .............................................................. 381/72
See application file for complete search history.

(56) References Cited

U.S. PATENT DOCUMENTS

| | | | | |
|---|---|---|---|---|
| 2007/0044206 | A1* | 3/2007 | Sato | A61F 11/14<br>2/209 |
| 2007/0277995 | A1* | 12/2007 | Sakai | H04R 1/1033<br>174/113 R |
| 2014/0076626 | A1* | 3/2014 | Wang | H01B 7/40<br>174/84 R |
| 2015/0281823 | A1* | 10/2015 | Taylor | H04R 1/1033<br>381/384 |
| 2018/0250168 | A1* | 9/2018 | Herring | H04R 1/1016 |
| 2020/0213708 | A1* | 7/2020 | Wang | H04R 1/1066 |

FOREIGN PATENT DOCUMENTS

| | | | | |
|---|---|---|---|---|
| GB | 2279202 A | * 12/1994 | A61F 11/14 |
| JP | S49-81137 | * 7/1974 | H04R 1/10 |
| WO | 2016200950 A2 | 12/2016 | |
| WO | 2018057907 A1 | 3/2018 | |

OTHER PUBLICATIONS

Partial International Search for PCT International Application No. PCT/IB2021/050250, mailed on Apr. 22, 2021, 10 pages.

* cited by examiner

CABLE COMPACTION SYSTEM FOR PROTECTIVE PERSONAL EQUIPMENT

CROSS REFERENCE TO RELATED APPLICATIONS

This application is a national stage filing under 35 U.S.C. 371 of PCT/IB2021/050250, filed Jan. 14, 2021, which claims the benefit of U.S. Provisional Application No. 62/963,765, filed Jan. 21, 2020, the disclosure of which is incorporated by reference in its/their entirety herein.

BACKGROUND

The use of hearing devices are well known. Many hearing devices involve an antenna configured to receive radio frequencies (RF) which is then demodulated to produce (possibly with other information) a sound signal that can be provided to a user through a speaker. Hearing devices often come in the form of in-ear plugs or over-the-ear headsets. Sound quality and consistency have been issues facing construction of new hearing devices.

SUMMARY

A hearing protection device is provided. The hearing protection device includes a first earmuff connected to a second earmuff by a connector. Each of the first and second earmuffs are configured to receive an ambient sound and provide a dampened ambient sound to a wearer. The connector also includes a cable connection path with a cable connection mechanism that receivably couples a cable to the connector.

The advantage of such a hearing device is that more flexibility is achieved for placing the earmuffs relative to the wearer's ears and that the earmuffs can be placed independent of the connector or headband.

BRIEF DESCRIPTION OF THE DRAWINGS

The drawings illustrate generally, by way of example, but not by way of limitation, various embodiments discussed in the present document.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "hearing device" is understood to include earmuffs and earplugs.

The term "connector" is to be understood to mechanically connect the hearing devices or earmuffs of the hearing protector.

The term "releasably connected" is to be understood that the cable is coupled to the connector by the connection assembly such that the coupling can be released and the cable can be moved away from the connector.

A problem with existing hearing device may be if these are worn with other protective equipment such as helmets or the like. This may lead to a situation, where the earmuffs of such a hearing device are difficult to place correctly relative to the wearer's ears. This may lead to reducing the effectiveness of the protective equipment and may even endanger the wearer relative to hearing damage.

It is therefore an object of the present disclosure to overcome these disadvantages and to provide a hearing device with increased flexibility with regard to placing the earmuffs relative to the wearer's ears.

Figure 1:
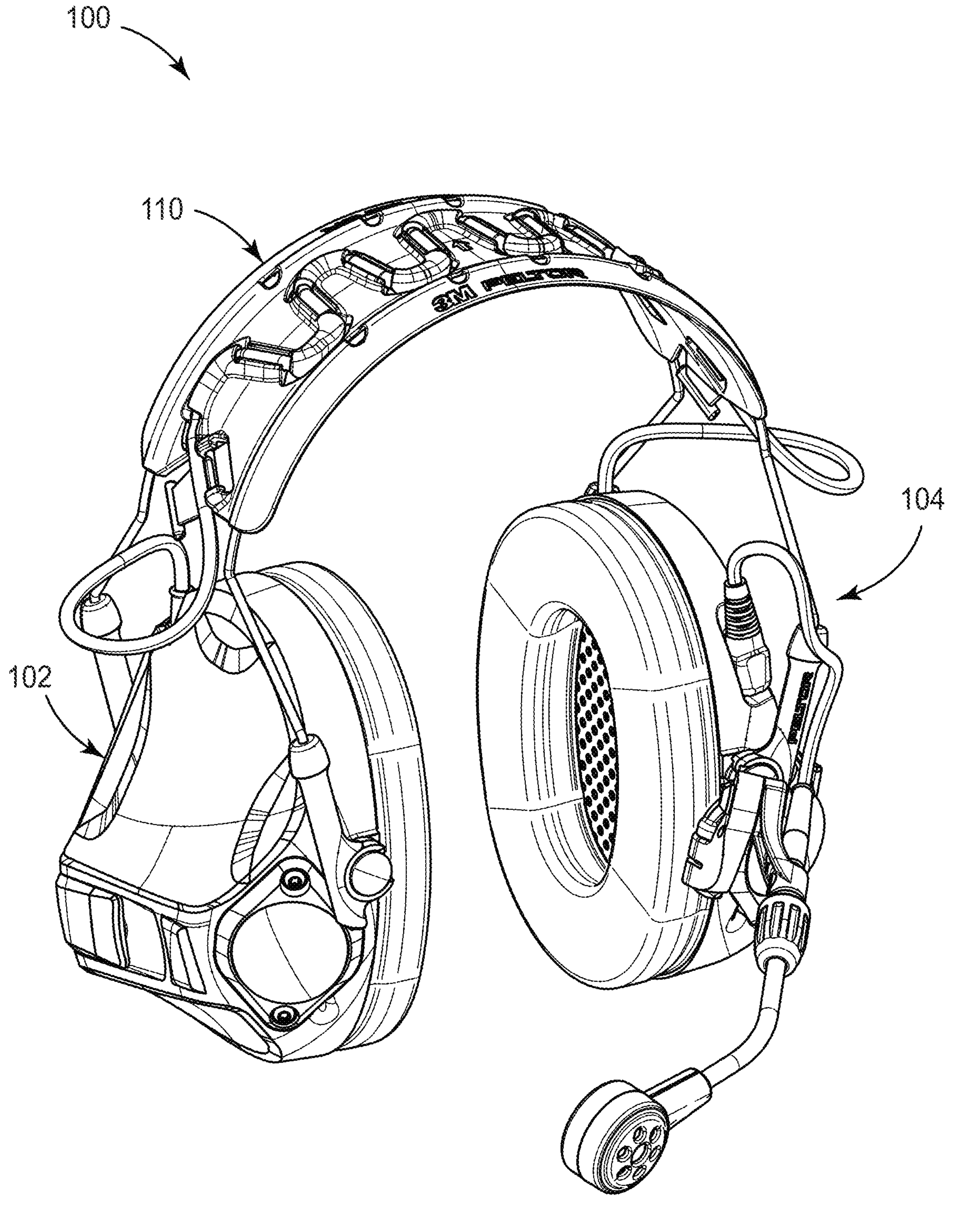
FIG. 1 illustrates a prior art personal protective headset.

FIG. 1 illustrates a prior art personal protective headset. Headset 100 includes two over-the-ear hearing protection devices 102 and 104 connected by a headband 114. Hearing protector devices 102, 104 are mechanically connected by headband 110, which may also include padding (not shown) for user comfort. The mechanical connection may include one or more metallic spring wires (not shown) to keep hearing protection devices 102, 104 in place by applying a certain pressure to the human head. The spring wires can be supported by a sheet of metal or plastic encased in a soft material which also acts like a cushion to enhance comfort for the user while wearing headset 100.

Each hearing protector device 102 includes a microphone (not shown), which in a preferred embodiment may be configured such that wind noise is reduced. Additionally, each hearing protector device 102 may in a preferred embodiment also include cushioning which may be configured to both increase user comfort and dampen ambient sounds.

Device 100 may include control circuitry such as storage and processing circuitry. Storage and processing circuitry may include storage such as nonvolatile memory (e.g., flash memory or other electrically-programmable-read-only memory configured to form a solid-state drive), volatile memory (e.g., static or dynamic random-access-memory), etc. Processing circuitry in storage and processing circuitry may be used to control the operation of device 100. This processing circuitry may be based on one or more microprocessors, microcontrollers, digital signal processors, baseband processor integrated circuits, application specific integrated circuits, or other such devices as known to those practiced in the art.

Storage and processing circuitry may be used to run software on device 100. The software may handle communications, may process sensor signals and take appropriate action based on the processed sensor signals (e.g., to turn on or off functions in device 100, to start or stop audio playback, etc.), and may handle other device operations. To support interactions with other PPE equipment, storage and processing circuitry 16 may be used in implementing communications protocols. Communications protocols that may be implemented using storage and processing circuitry include wireless local area network protocols (e.g., IEEE 802.11 protocols—sometimes referred to as WiFi® and WiGig), protocols for other short-range wireless communications links such as the Bluetooth® protocol, cellular telephone protocols, as well as others known to those practiced in the art. For example, the protocol described in WO 2016/200950, published on Dec. 15, 2016, which is incorporated herein by reference, may be used in some embodiments.

Device 100 may also have an antenna (not shown) configured to receive wireless radio signals. Device 100 also has a PCB board (not shown). Power to components of device 100 is provided by a power source, such as a battery (not shown).

Device 100 may include microphones, speakers, tone generators, and other audio components. Microphones may gather voice signals and/or ambient noise signals. Speakers may play back sound for a user either at ambient levels or after being processed by control circuitry.

Device 100 may include also include a power source such as a battery, for example, to provide power to the circuitry of device 100. The battery may be a rechargeable battery, chargeable either in a wired or wireless configuration.

Figure 2A:
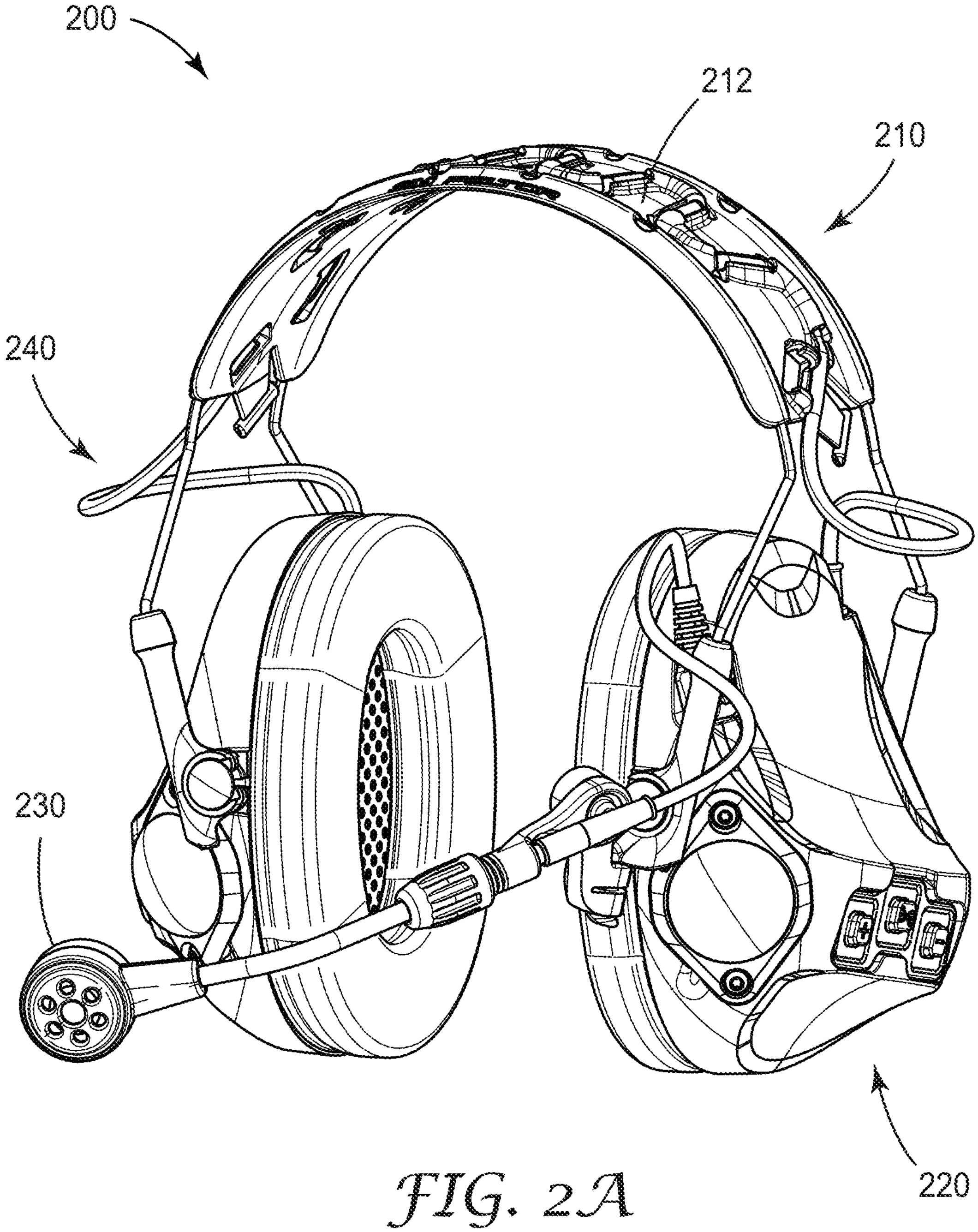
FIGS. 2A-2C illustrate a personal protective headset in accordance with an embodiment of the present invention.
Figure 2B:
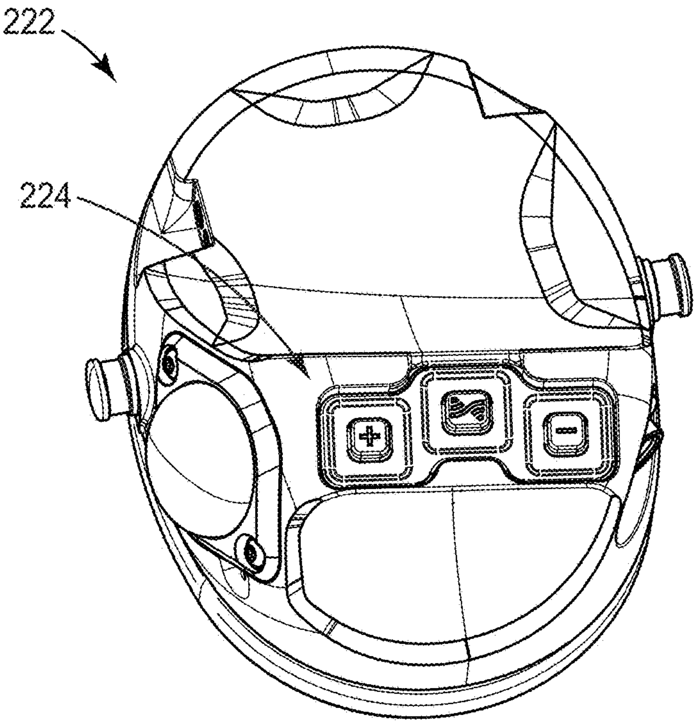
Figure 2C:
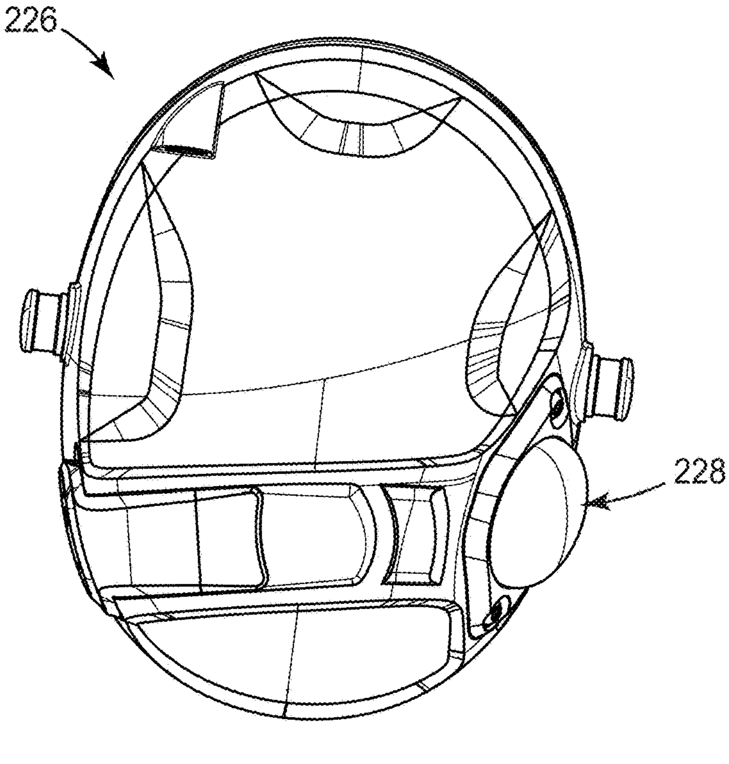

FIGS. 2A-2C illustrate a personal protective headset in accordance with an embodiment of the present invention. FIG. 2A illustrates a personal protective headset 200 with a connector 210 that connects a pair of earmuffs 220. Headset 200 also includes a microphone 230.

A cable 240 couples a first earmuff 220 to a second earmuff 220. In some embodiments, headset 200 is designed to be compatible with both a helmet configuration and a headband configuration. However, in some embodiments a helmet configuration requires a longer cable 240. In the helmet configuration, cable 240 is designed to run along an interior of the helmet. In some embodiments, cable 240 is designed to fit under the shell and padding at a back portion of a helmet. However, cable 240 may also be configured, in other embodiments, to run on an outer shell of a helmet. The helmet configuration may require fasteners to hold cable 240 in place. Therefore, in a headband configuration, it is desired for the extra length of cable 240 to be compressed in a storage configuration such that a user experience is not affected. The cable compaction assembly, therefore, must be designed such that it is convenient to move cable 240 between a compressed assembly and an open assembly.

FIGS. 2B and 2C illustrate other features of a personal protective headset assembly, including first and second earmuff housings 222, 226 which house electronics associated with sound compression operations. A first earmuff 222, in one embodiment, includes volume controls 224 that are designed to be more convenient for a user, such that the volume increase and decrease buttons are more easily identifiable both by the arrangement of the buttons and the raised functional indicators.

Figure 3:
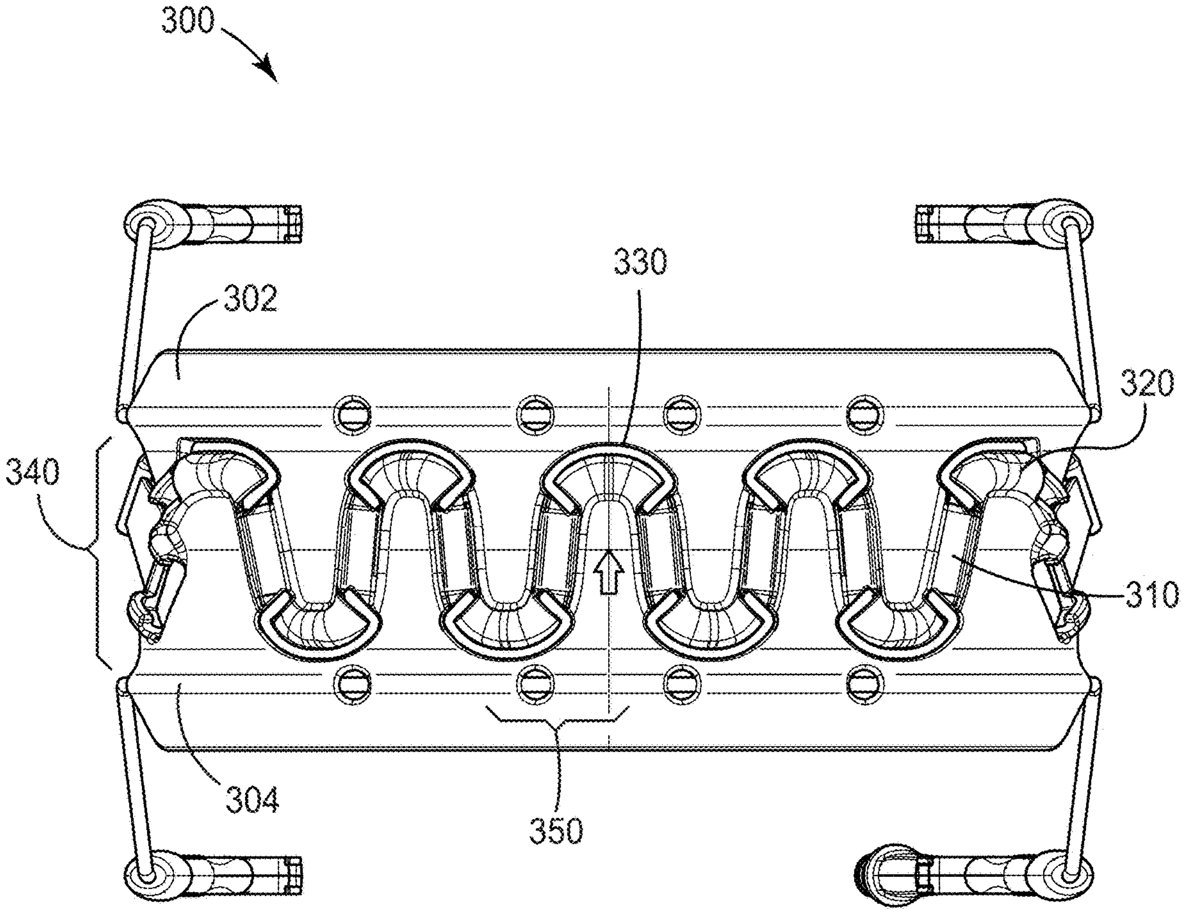
FIG. 3 illustrates a view of a cable compaction system in accordance with an embodiment of the present invention.

FIG. 3 illustrates a view of a cable compaction system in accordance with an embodiment of the present invention. Cable compaction system 300, in one embodiment, is formed to interact with a connector (e.g. connector 210) that can function in either a headband configuration or a helmet configuration. The connector may comprise one or more metallic spring wires, or other suitable mechanisms configured to maintain pressure between the earmuffs and a user's head. Cable compaction system 300 may include a molded assembly 302 that fits over, or receives, the metallic spring wires, as illustrated in FIG. 3. A cable 310 interacts with a plurality of compaction features 320. As illustrated in FIG. 3, in one embodiment, cable 310 is wound in a sinusoidal shape by alternatingly interacting with compaction features 320 on a first side 304 and a second side 302 of compression assembly 300.

Cable compaction system 300, in one embodiment, is a molded plastic component. For example, but not by limitation, cable compaction system 300 may be made from a thermoplastic elastomer (TPE), ethylene propylene diene monomer (EPDM), or nitrile rubber (NBR). However, cable compaction system 300 may also be formed of fabric, metal, or another suitable material in other embodiments. Plastic may be preferred for comfort as many use environments may include a range of temperatures. However, other suitable materials may also be used. Cable compaction system 300, in one embodiment, is sufficiently stiff to maintain positions of compaction features 320 and cable 340. However, cable compaction system 300, in some embodiments, has some flexibility.

Cable compaction features 320, in one embodiment, have a snap connection such that cable 340 is snapped into place in each cable compaction feature 330. In another embodiment, cable compaction features 320 are placeholders that cable 340 is wound around. Other mechanical, releasable feature designs are also contemplated. For example, cable 340 may be coated in a magnetic material that removably couples to one or more points on compression system 300. Cable 340 may also have either a hook or loop attachment on part or all of its surface that couples to a corresponding loop or hook portion on a surface of compression system 300. Other suitable fastening mechanisms are also expressly contemplated.

Compaction features 320, in one embodiment are formed as an extension of system 300, for example during a molding process. In another embodiment, compaction features 320 are fixed to compression system 300, using a permanent fastening mechanism such as an adhesive, welding, etc.

Cable 340 has a total length that is longer than a total length of system 300. Cable compaction system 300 compresses a length footprint of at least a portion of cable 340 such that it fits on cable compaction system 300. As illustrated in FIG. 3, compression is completed by winding cable 340 in a sinusoidal meander pattern between first side 302 and second side 304. Connectors 330 are alternatively placed along first and second sides 302, 304 such that cable 340 winds around the exterior of each connector 330, creating a sinusoidal pattern with a period 350 and an amplitude 340.

FIGS. 4-7 illustrate alternative cable compaction system arrangements in accordance with embodiments of the present invention. While FIG. 3 illustrates one compressed cable arrangement of a sinusoidal meander pattern, other patterns are expressly contemplated, such as those illustrated in FIGS. 4-7. Connection features are not explicitly shown in FIGS. 4-7, but could be any of the mechanical connection features described herein.

Figure 4:
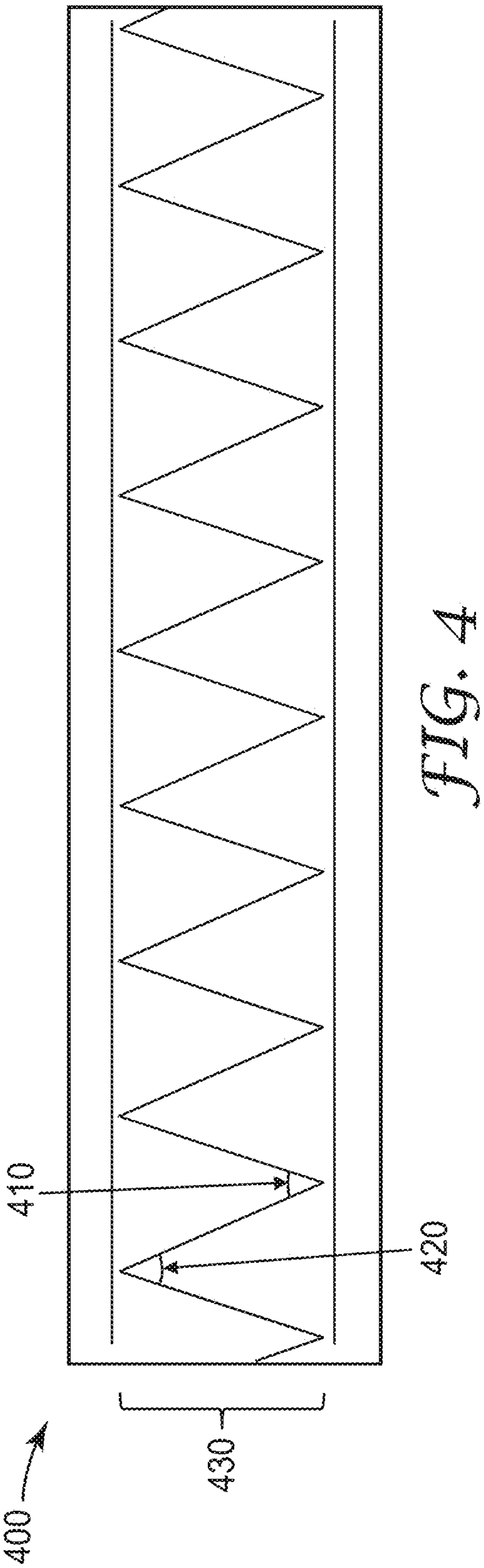
FIGS. 4-7 illustrate alternative cable compaction system arrangements in accordance with embodiments of the present invention.

FIG. 4 illustrates a schematic of a compression system 400 where a cable experiences sharp turns around compaction features, creating a zig-zag or angular pattern with an amplitude 430 and first and second angles 410, 420. First and second angles 410, 420 may be the same, or substantially the same, as illustrated in FIG. 4. Alternatively, they may differ, as illustrated in FIG. 5.

Figure 5:
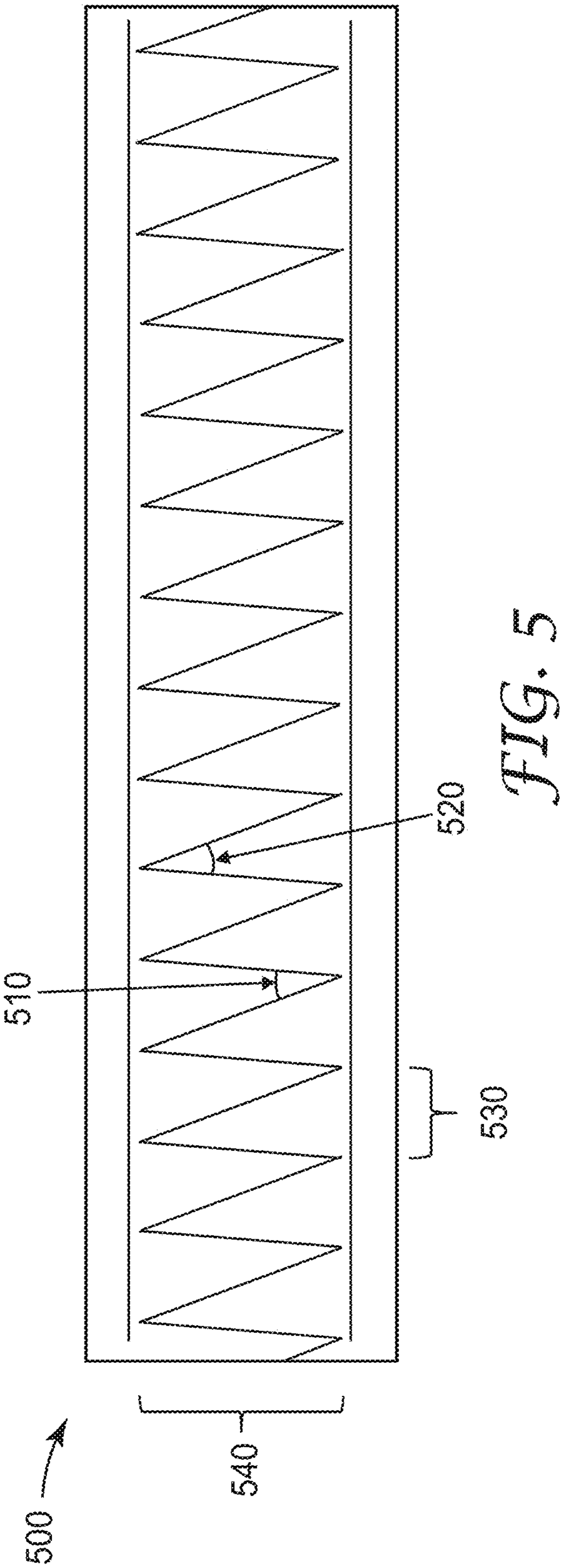

FIG. 5 illustrates a compression system 500 where a cable experiences sharp turns around compaction features, creating a zig-zag or angular pattern with an amplitude 540 and triangular widths 530. First angle 510 and second angle 520 differ, in contrast to the design of FIG. 4.

Figure 6:
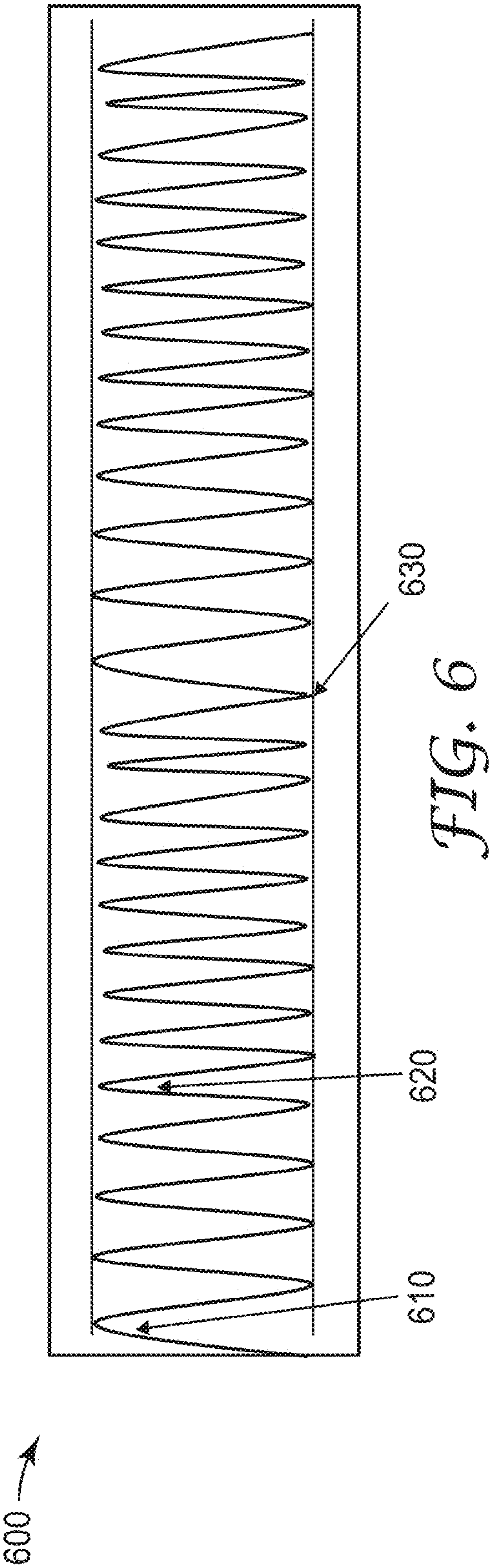

FIG. 6 illustrates a compression system 600 where a cable is in an irregular meander pattern with different curvature, such as curvature 610 and curvature 620. Cable may also experience one or more sharp turns 630.

Figure 7:
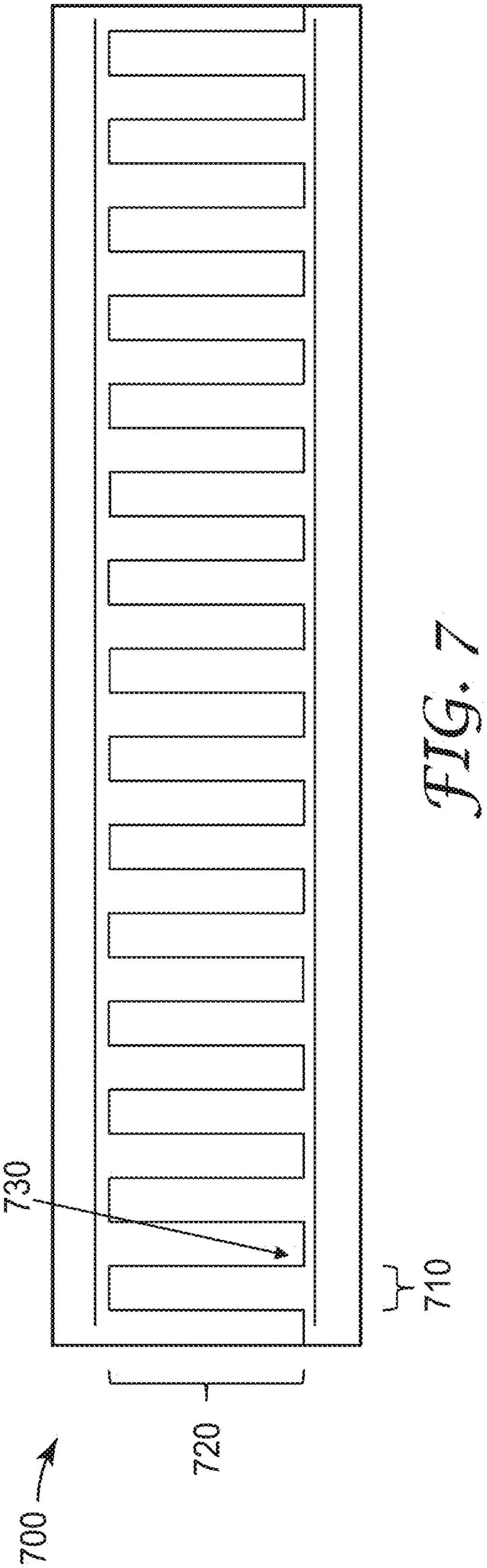

FIG. 7 illustrates a compression system 600 where a cable curves around rectangular compaction features, resulting in curves with width 710 and height 720. However, while a rectangular meander pattern is illustrated, with right angles 730, it is expressly contemplated that some curvature may be present at least in part caused by a width of a cable. Additionally, in some embodiments, sharp turns are avoided in order to reduce strain on a compressed cable, which may cause the cable to crack or break prematurely.

Figure 8A:
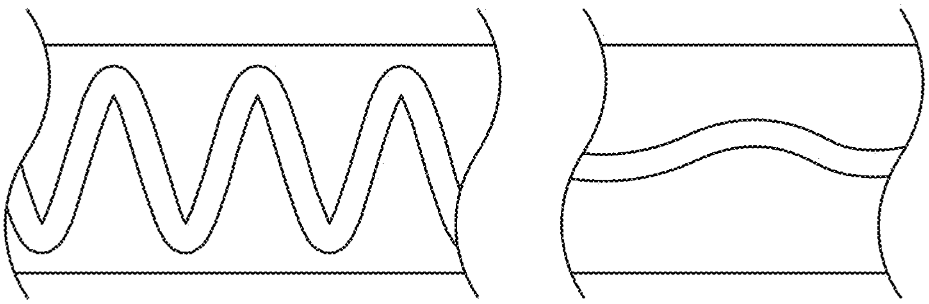
FIGS. 8A and 8B illustrate cable compaction systems in the form of a meander.
Figure 8B:
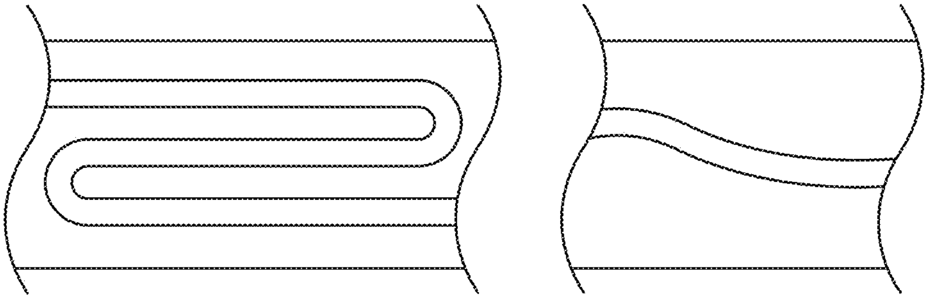

FIGS. 8A and 8B illustrate cable compaction systems in the form of a meander. FIG. 8A shows a first arrangement of the excess length portion of the connection cable in the form of a meander, and the transition of the cable to a released stage. The meander of FIG. 8B may be referred to as a width-wise meander, where a cable is wound back and forth along a width of the connection assembly.

FIG. 8B shows another arrangement of the excess length portion of the connection cable in the form of a meander different to the meander shown in FIG. 8A, as well as the transition to a released stage. The meander of FIG. 8B may be referred to as a length-wise meander, where a cable is wound back and forth along a length of the connection assembly.

Figure 9A:
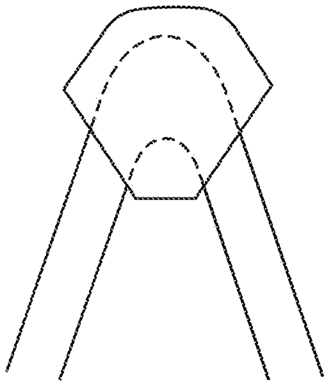
FIGS. 9A and 9B illustrate a first embodiment of a fastener for holding the connection cable in place.
Figure 9B:
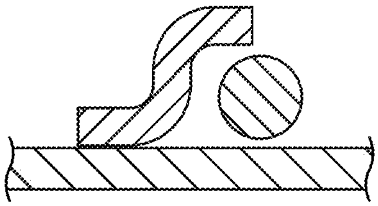

FIGS. 9A and 9B illustrate a first embodiment of a fastener for holding the connection cable in place. FIG. 9A shows a first embodiment of the fastening means for holding the connection cable in place. FIG. 9B shows a cross-sectional side view of the fastening means according to FIG. 9A.

Figure 10A:
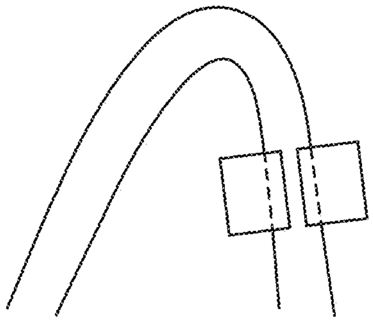
FIGS. 10A and 10B illustrate a second embodiment of a fastener for holding the connection cable in place.
Figure 10B:
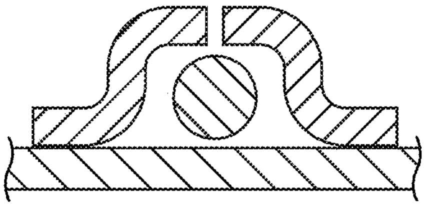

FIGS. 10A and 10B illustrate a second embodiment of a fastener for holding the connection cable in place. FIG. 10A shows a second embodiment of the fastening means for holding the connection cable in place. FIG. 10B shows a cross-sectional side view of the fastening means according to FIG. 10B.

Figure 11A:
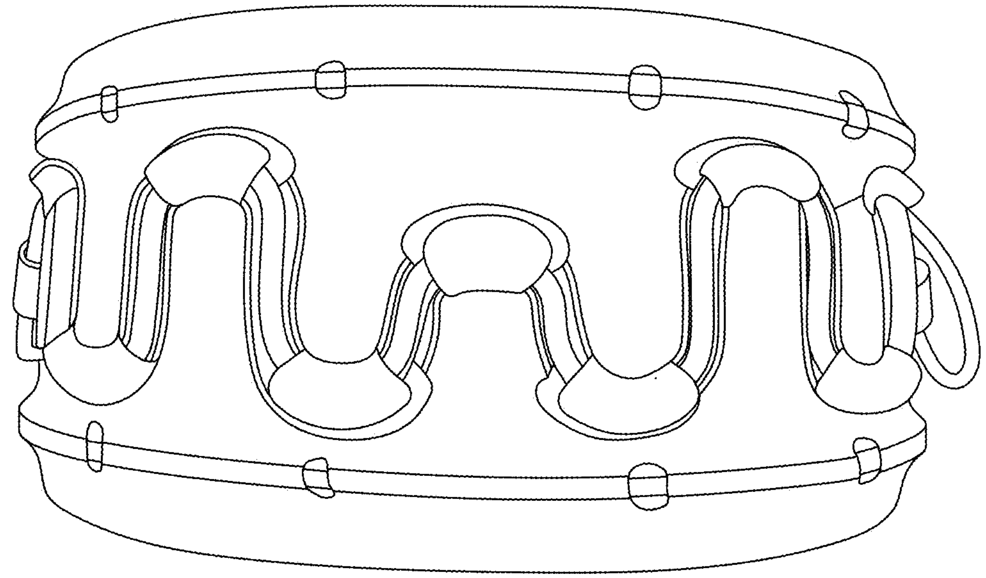
FIGS. 11A-11D illustrate views of an embodiment of a cable compaction assembly in the form of a meander.

FIGS. 11A-11D illustrate views of an embodiment of a cable compaction assembly in the form of a meander. FIG. 11A shows a headband of the hearing protector having an excess length portion in the form of a meander releasably hold in place by fastening means.

Figure 11B:
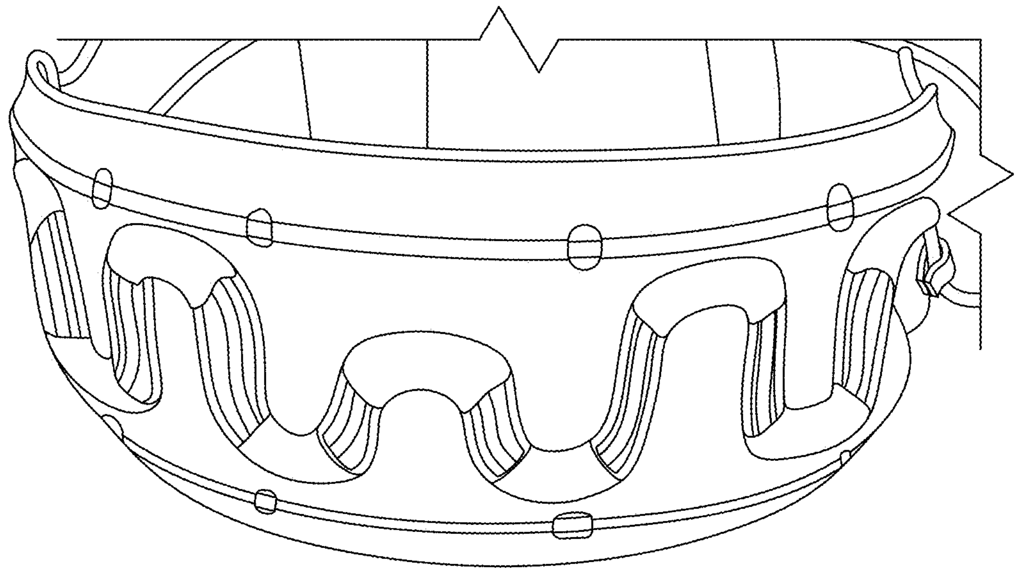
Figure 11C:
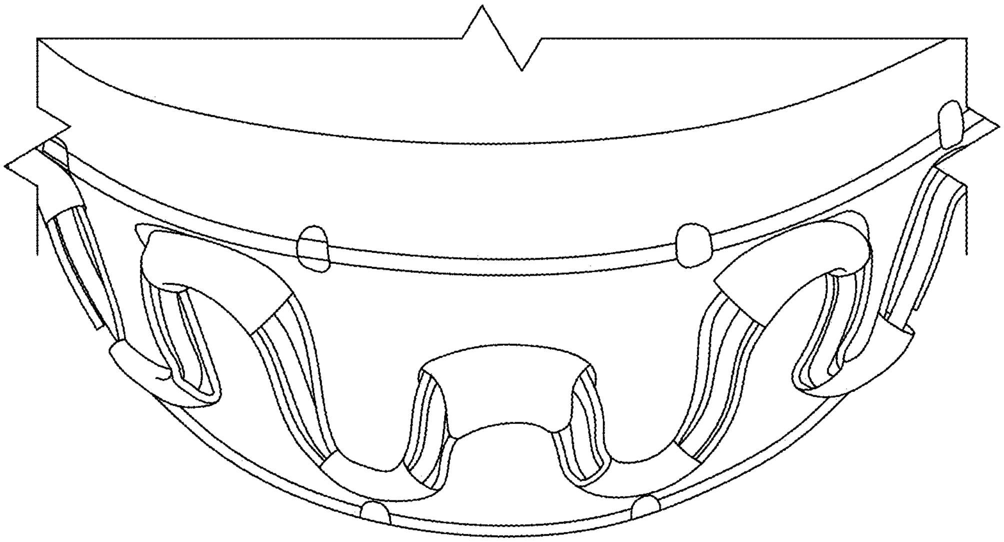
Figure 11D:
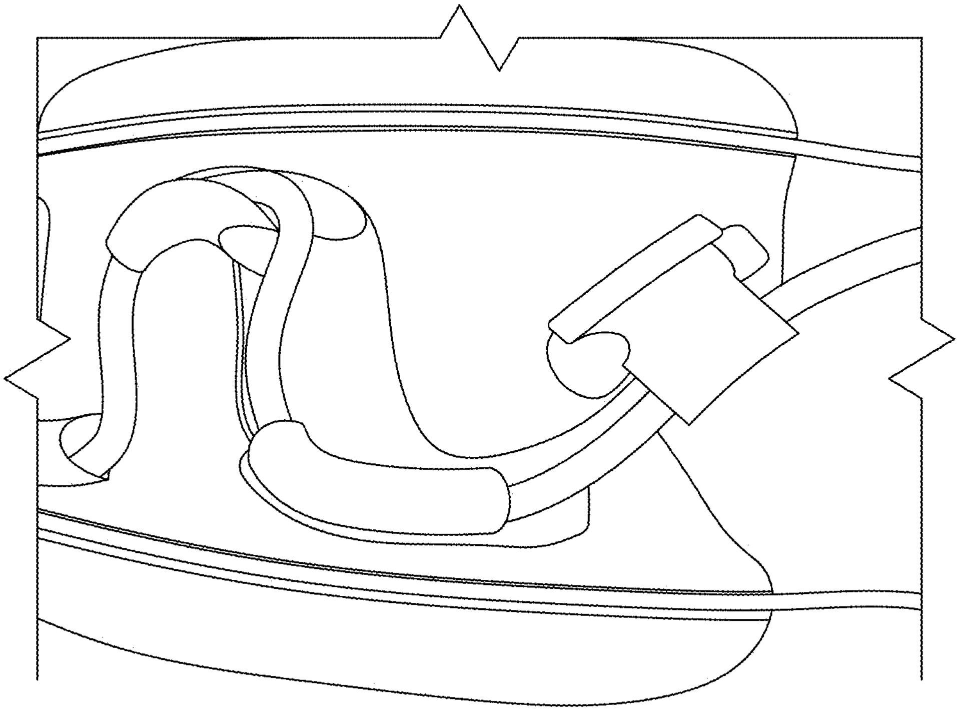

FIGS. 11B and 11C show the fastening means of FIG. 11A in more detail, whereas the fastening means are open on one side and are attached to the headband on the opposite side. FIG. 11D shows a second fastening means formed by a closed loop holding the connection cable adjacent to an end of the headband.

Figure 12A:
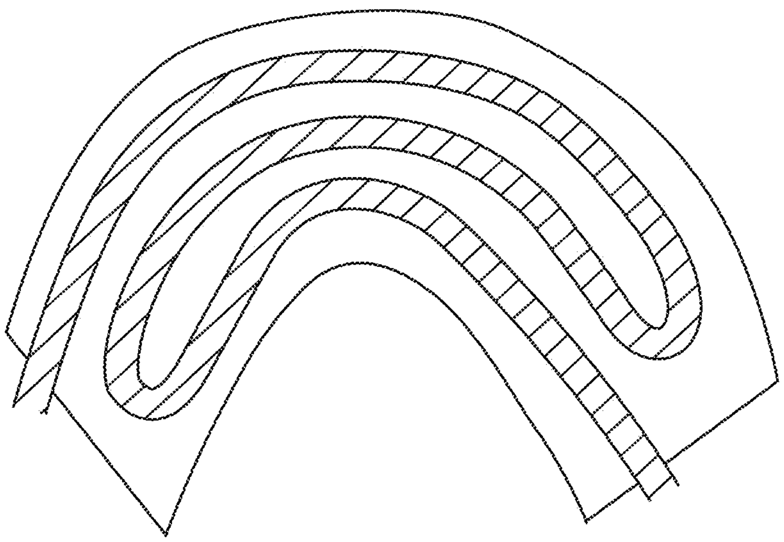
FIGS. 12A and 12B illustrate views of an embodiment of a cable compaction assembly in the form of a lengthwise meander.
Figure 12B:
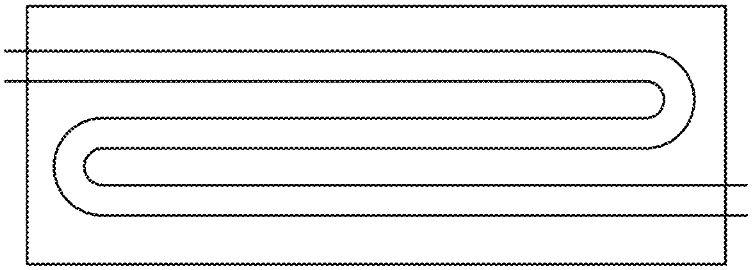

FIGS. 12A and 12B illustrate views of an embodiment of a cable compaction assembly in the form of a lengthwise meander. FIG. 12A shows in a top perspective view another embodiment of the excess length portion of the connection cable attached to the headband of the hearing protector in a curved configuration. FIG. 12B shows the embodiment as shown in FIG. 12A in a flat configuration.

Figure 13:
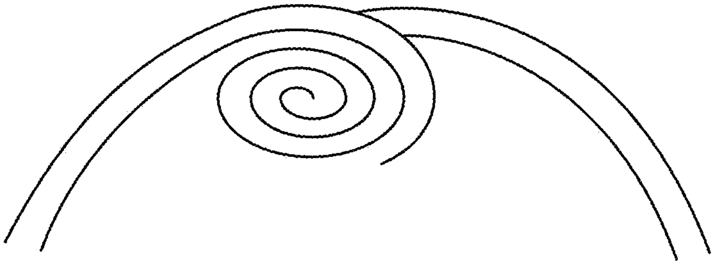
FIG. 13 illustrates an embodiment of a cable compaction assembly in the form of a coil.

FIG. 13 illustrates an embodiment of a cable compaction assembly in the form of a coil. FIG. 13 shows another embodiment of the excess length portion of the connection cable in the form of a coil.

A hearing protection device is presented. The device has a first earmuff connected to a second earmuff by a connector. Each of the first and second earmuffs are configured to receive an ambient sound and provide a dampened ambient sound to a wearer. The device also has a cable, with a cable length, that extends from the first earmuff to the second earmuff. The cable is coupled to the connector by a connection assembly. The connection assembly comprises a plurality of connection mechanisms arranged in a connection plan. Such a hearing protection device gives more freedom of placing the cable in a compact arrangement.

The cable length is longer than a length of the connector. The connection assembly allows for more freedom of compact placement of the cable.

The connection plan comprises the plurality of connection mechanisms arranged alternatively on a first side of the connector and a second side of the connector. This provides good mechanical properties when fixing the cable.

The plurality of connection mechanisms are fixed to the connector. Integral connection mechanisms provide for a compact design that is easy to manufacture and use.

The plurality of connection mechanisms are built into the connector. Built-in connection mechanisms provide for a compact design that is easy to manufacture and use.

The plurality of connection mechanisms are molded into the connector. Molded connection mechanisms provide for a compact design that is easy to manufacture and use.

The plurality of connection mechanisms are moveable with respect to the connector. Moveable connection mechanisms help to attach and release the cable without damage.

The plurality of connection mechanisms comprise a plurality of snap fit mechanisms configured to releasably receive the cable. Snap fit mechanisms allow for easy and reliable coupling and decoupling of the cable.

Each of the plurality of connection mechanisms has a radius of curvature. The radius of curvature avoids sharp edges and maintains a minimum cable bend radius.

The earmuffs are removable from the connector. Removable earmuffs allow for more flexibility in their placement.

The hearing protection device is, in a first mode, coupled to a headband and, in a second mode, coupled to a helmet. Different modes allow for appropriate use of hearing protectors when a helmet is needed.

A hearing protector is presented. The hearing protector includes two earmuffs and a headband mechanically connecting the earmuffs. The hearing protector further also includes a connection cable electrically connecting electronic components within the two earmuffs and first guiding mechanism for guiding the connection cable along the headband. The connection cable is releasably attached to the first guiding mechanism. The connection cable further comprises an excess length portion of connection cable stored at the headband and further comprising a second guiding mechanism formed by a closed loop.

The earmuff are detachable from the headband.

The excess cable length is provided by a portion of the connection cable arranged in a meander shape or a coiled shape.

The meander shape or the coiled shape is releasable such that the meander shape or the coiled shape is turned into a substantially straight shaped cable portion.

The guiding mechanism comprise mechanical fasteners selected from hooks, hook and loop fasteners, indents, clips and/or flaps.

The connection cable is clamped by the guiding mechanism.

A method of increasing the length of a connection cable in a hearing protector is presented. The method includes providing a hearing protector comprising two earmuffs and a headband mechanically connecting the earmuff. The hearing protector further comprising a connection cable electrically connecting electronic components within the two earmuffs and guiding mechanism for guiding the connection cable along the headband. The connection cable is releasably attached to the guiding mechanism. The method also includes providing an excess length portion of connection cable. The method also includes storing the excess length portion at the headband. The method also includes releasing the excess length portion from the headband thereby increasing the effective length of the connection cable between the earmuffs.

A cable compaction system is presented. The cable compaction system includes a cable compaction assembly with an assembly length. The system also includes a plurality of compaction features arranged in a pattern on the cable compaction assembly. The plurality of compaction features are each configured to receive a portion of a cable such that a cable length is compacted to the assembly length. A cable compaction system may accommodate a total length of cable needed for a hearing protection system in both a headset and a helmet mode by storing the cable conveniently in the headset mode, but allowing it to be releasably available for a helmet mode.

The pattern causes the cable to form a meander pattern when received by the plurality of compaction features.

The meander pattern is a sinusoidal pattern.

The meander pattern is a lengthwise meander pattern.

The meander pattern is a widthwise meander pattern.

What is claimed is:

1. A hearing protection device comprising:

a first earmuff connected to a second earmuff by a connector, wherein each of the first and second earmuffs are configured to receive an ambient sound and provide a dampened ambient sound to a wearer; and a cable, with a cable length, that extends from the first earmuff to the second earmuff, wherein the cable is coupled to the connector by a connection assembly and wherein the connection assembly comprises a plurality of connection mechanisms arranged alternatively on a first side of the connector and a second side of the connector, wherein the plurality of connection mechanisms each comprise curvature, wherein the plurality of connection mechanisms comprise a plurality of snap fit mechanisms configured to releasably receive the cable, wherein the plurality of snap fit mechanisms at least partially enclose the cable.

2. The hearing protection device of claim 1, wherein the cable length is longer than a length of the connector.

3. The hearing protection device of claim 1, wherein the plurality of connection mechanisms are fixed to the connector.

4. The hearing protection device of claim 3, wherein the plurality of connection mechanisms are built into the connector.

5. The hearing protection device of claim 3, wherein the plurality of connection mechanisms are molded into the connector.

6. The hearing protection device of claim 1, wherein the plurality of connection mechanisms are moveable with respect to the connector.

7. The hearing protection device of claim 1, wherein the hearing protection device is, in a first mode, coupled to a headband and, in a second mode, coupled to a helmet.

8. The hearing protection device of claim 1, wherein each of the plurality of connection mechanisms has a radius of curvature that maintains a cable bend radius.

9. A cable compaction system comprising:

A cable compaction assembly with an assembly length;

a plurality of compaction features arranged in a pattern on the cable compaction assembly, wherein the pattern causes the cable to form a meander pattern when received by the plurality of compaction features; and wherein the plurality of compaction features are each configured to receive a portion of a cable such that a cable length is compacted to the assembly length, and wherein the plurality of compaction features are free of sharp edges;

wherein the plurality of compaction features each comprise curvature, wherein the plurality of compaction features comprise a plurality of snap fit mechanisms configured to releasably receive the cable, wherein the plurality of compaction features at least partially enclose the cable.

10. The cable compaction system of claim 9, wherein the meander pattern is a sinusoidal pattern.

11. The cable compaction system of claim 9, wherein the meander pattern is a lengthwise meander pattern.

12. The cable compaction system of claim 9, wherein the meander pattern is a widthwise meander pattern.

* * * * *